United States Patent [19]
Pritchard et al.

[11] Patent Number: 5,380,300
[45] Date of Patent: Jan. 10, 1995

[54] DOUCHE NOZZLE

[75] Inventors: Robert W. Pritchard, Pittsburgh; Lawrence J. Stuppi, Bellevue, both of Pa.

[73] Assignee: SmithKline Beecham, Philadelphia, Pa.

[21] Appl. No.: 109,178

[22] Filed: Aug. 19, 1993

[51] Int. Cl.6 ............................................. A61M 31/00
[52] U.S. Cl. ............................................................ 604/275
[58] Field of Search .................. 604/54, 55, 212–215, 604/275–279, 268, 126

[56] References Cited

U.S. PATENT DOCUMENTS

| | | | |
|---|---|---|---|
| 128,257 | 6/1872 | Snyder | 604/275 |
| 177,632 | 5/1876 | Gassin et al. | 604/275 |
| 205,353 | 6/1878 | Chamberlin . | |
| 1,534,852 | 4/1925 | Hunter | 604/275 |
| 1,824,808 | 10/1928 | Findley . | |
| 2,122,234 | 10/1936 | McAuliffe . | |
| 2,147,158 | 9/1937 | Goldenthal . | |
| 2,199,844 | 5/1940 | Tucker | 604/275 |
| 2,484,290 | 10/1949 | Handel | 604/275 |
| 2,543,075 | 2/1951 | Swain | 604/275 |
| 2,610,627 | 9/1952 | Watt et al. | 604/275 |
| 3,225,763 | 12/1965 | Waterman | 604/275 |
| 3,228,396 | 1/1966 | Potts et al. | 604/275 |
| 3,512,526 | 11/1967 | Fielding . | |
| 3,968,797 | 7/1976 | Packer et al. . | |
| 4,167,186 | 9/1979 | Pick et al. . | |
| 4,309,995 | 1/1982 | Sacco . | |
| 4,318,403 | 3/1982 | Sneider . | |
| 4,351,336 | 9/1982 | Sneider . | |
| 4,519,794 | 5/1985 | Sneider . | |

Primary Examiner—C. Fred Rosenbaum
Assistant Examiner—Frank Wilkens, III
Attorney, Agent, or Firm—Nora Stein-Fernandez; Stuart R. Suter; Edward T. Lentz

[57] ABSTRACT

A douche nozzle has an internal baffle member for regulating the flow of liquid exiting the nozzle. The nozzle may be provided with spaced apart grooves on its exterior surface extending from the distal end of the nozzle to and across an internally threaded open base.

2 Claims, 2 Drawing Sheets

DOUCHE NOZZLE

The present invention relates to a douche nozzle for use with a squeeze bottle filled with a liquid.

Disposable douche products are in widespread commercial use. These products comprise a douche nozzle and a sealed plastic squeeze bottle filled with a douching liquid. After the bottle is opened, the douche nozzle is fastened to the bottle and the douching liquid is dispensed through the nozzle by squeezing the bottle.

The present invention provides an improved douche nozzle that affords more convenient, comfortable and efficient douching. In particular, the present invention provides a douche nozzle that includes a baffle member for regulating the flow of liquid dispensed by the douche nozzle.

Thus, the present invention provides a douche nozzle for dispensing a liquid, comprising an elongated hollow tubular body having an open proximal end and a distal end, a plurality of apertures through the tubular body adjacent the distal end to permit liquid flowing through the interior of the tubular body toward the distal end to exit the nozzle, and an elongated baffle member arranged inside the tubular body adjacent the apertures, the baffle member being operable to regulate the flow of liquid exiting the nozzle.

In a preferred embodiment of the invention, the nozzle has an internally threaded base portion for attachment to a squeeze bottle, and plurality of grooves are formed in the exterior of the nozzle extending longitudinally across the base portion to the distal end of the nozzle.

The present invention is illustrated in terms of its preferred embodiment in the accompanying drawings in which:

FIG. 1 is a side elevational view of the douche nozzle of the invention;

FIGS. 2 and 3 are views in section taken along lines 2—2 and 3—3, respectively, in FIG. 1;

FIG. 4 is a side elevational view of the baffle member used in the present invention;

FIGS. 5 and 6 are views in section taken along lines 5—5 and 6—6 in FIG. 4, respectively;

Figure 1:
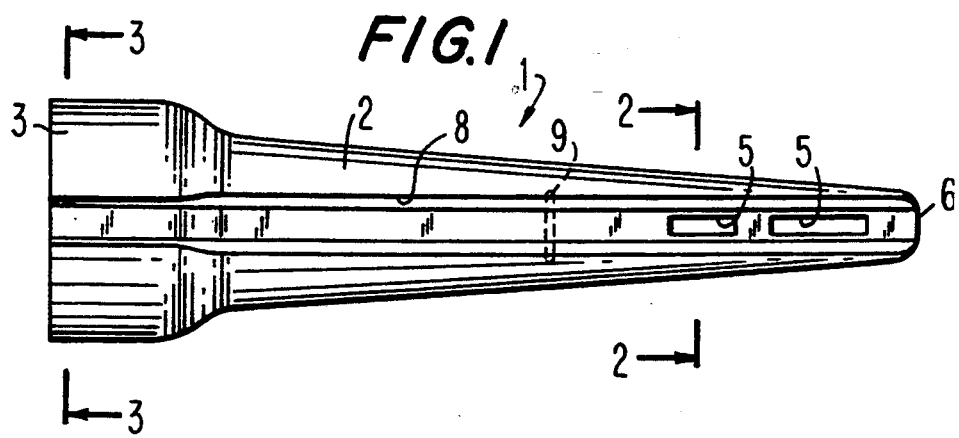
Figure 2:
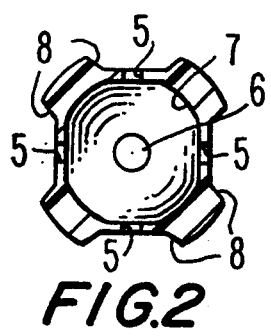
Figure 3:
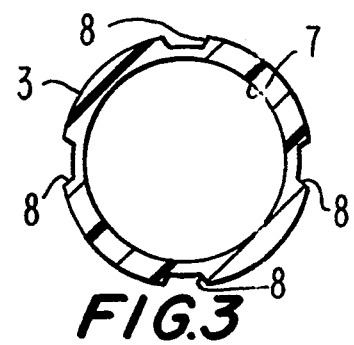

Referring to FIG. 1, the douche nozzle 1 is in the form of an elongated tubular body 2 having an open proximal end 3 formed with internal threads 4 (FIG. 7) for attaching the nozzle 1 to a conventional squeeze bottle (not shown). Alternatively, the end 3 may be provided with an internal groove (not shown) for snap fitting the nozzle 1 onto the squeeze bottle.

A plurality of slots 5 are arranged adjacent the distal end 6 to permit liquid flowing through the passageway 7 (FIG. 7) to exit the nozzle 1. The exterior of the tubular body 2 is provided with four longitudinally extending recessed grooves 8, the slots 5 being provided within the grooves 8. Grooves 8 extend from the distal end 6, across the body 2 and across the internally threaded proximal end or base 3.

Figure 4:
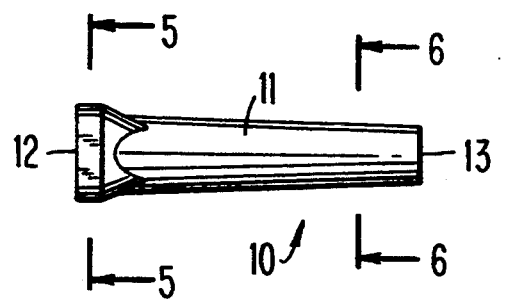
Figure 5:
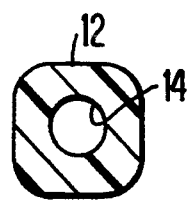
Figure 6:
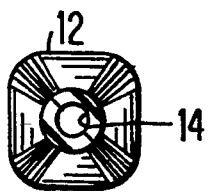

The baffle member 10 (FIG. 4) has an elongated tubular porous body 11 having an open proximal end or base 12 and a closed distal end 13. Tubular porous body 11 is preferably tapered so as to readily fit into the tapered tubular body 2 of nozzle 1. However, porous body 11 need not be tapered so long as it fits within body 2. Further, body 2, while preferably tapered, can be of uniform cross-section. If desired, the baffle member may be contoured to the shape of nozzle 1.

Baffle member 10 is provided with an internal passageway 14 through which liquid may flow from the base at the proximal end 12 to the distal end 13. Liquid escapes from passageway 14 through the voids and channels of the porous body 11 and, to some extent, through the porous closed distal end 13. Liquid flowing out of baffle member 10 in turn escapes from the nozzle 1 through slots 5.

Figure 7:
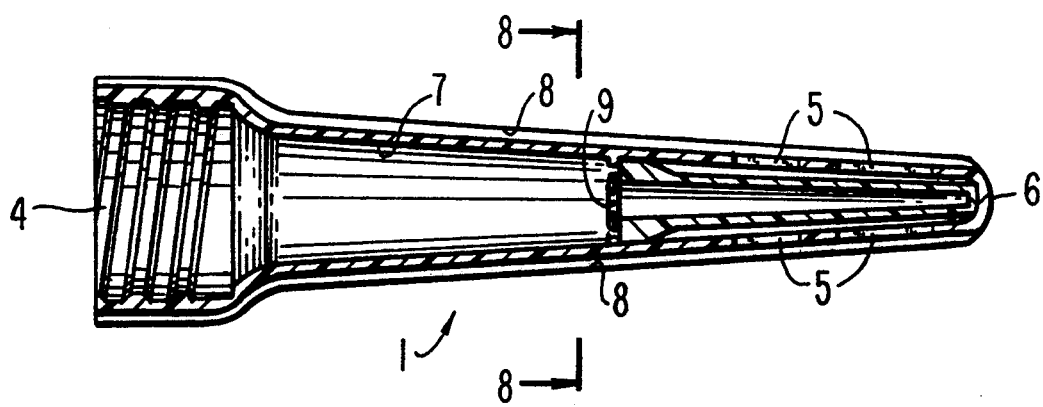
FIG. 7 is a side elevational view, in section, showing the assembly of the baffle member in the nozzle.
Figure 8:
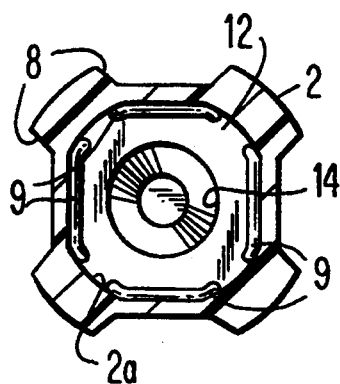
FIG. 8 is a view in section taken along lines 8—8 in FIG. 7.

Baffle member 10 is prevented from sliding to the right as viewed in FIG. 7 because the distal end 13 contacts the internal wall 2a of the distal end 6 of nozzle 1. Ribs 9 (FIG. 8) in the internal 2a wall of nozzle 1 prevent porous insert 10 from sliding to the left. Preferably, the base 12 of baffle member 10 has the same cross-section as and sealingly contacts inner wall 2a of the nozzle 1 so that liquid flowing through passageway 7 cannot bypass the passageway 14 in baffle member 10. In this way, all of the liquid flowing through nozzle 1 must pass through and be regulated by baffle member 10 before escaping via slots 5.

Figure 8A:
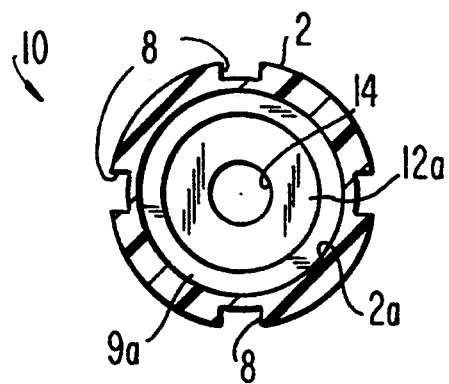
FIG. 8A is a view similar to FIG. 8 of another embodiment of the invention.

While nozzle 1 is shown with a generally square cross-section where the base 12 engages the inner wall 2a, other cross-sections are possible. For example, FIG. 8A shows an alternative embodiment of the invention where the baffle member 10 has a base 12a with a circular cross-section that sealingly engages the inner wall 2a, which is likewise of circular cross-section. In FIG. 8A the retaining rib 9a is in the form of a ring, rather than as spaced-apart ribs.

The nozzle 1 and baffle member 10 are assembled by sliding the member 10 through passageway 7 until base 12 passes beyond the ribs 9. Nozzle 1 as thus assembled is used in a conventional manner by attaching nozzle 1 to a squeeze bottle by means of threads 4. Liquid is dispensed from the bottle in a conventional manner by squeezing the bottle to expel the contents. Since base 12 of member 10 sealingly engages the inner wall 2a of nozzle 1, liquid flows through passageway 7 into passageway 14, thence diffuses through the porous body 11 of insert 10 and thence escapes in a regulated manner from nozzle 1 via slots 5.

Baffle member 10 accomplishes several purposes. Thus, member 10 diffuses the liquid before the liquid exits the nozzle, to ensure that the liquid exits the nozzle as gently flowing stream, even if excessive squeezing forces are exerted on the bottle. In the past, such excessive squeezing forces could result in a powerful spray. Baffle member 10 also acts as a barrier to minimize suckback of liquid into the nozzle from the vagina when the squeezing forces on the bottle are released.

Baffle member 10 may also be used to deliver a desired active agent along with the douching liquid. For example, member 10 may be impregnated with an active agent that is released into the douching liquid flowing through the baffle member. Suitable active agents may be introduced into the baffle member by impregnating the baffle member with a solution of the active agent followed by drying the baffle member. Alternatively, the baffle member may be impregnated with a solution of the active agent, the thus-impregnated member may be assembled into the nozzle, and the assembly enclosed within a hermetically sealed package to prevent the solution from drying out. Such techniques are known in the art of tampons, contraceptive sponges and other vaginal devices. See, e.g., U.S. Pat. Nos. 4,186,742, 4,613,497 and 5,070,889. A wide variety of active agents may be impregnated into the baffle member, such as antibiotics, anti-fungal agents, estrogenic steroids, progestational agents, and the like.

It is presently preferred that the nozzle 1 be provided with recessed grooves or channels 8 extending across the base or proximal end 3 to the distal end 6 of nozzle 1 to ensure that the douching liquid may readily drain out of the vagina.

Nozzle 1 may be made of any material suitable for forming to the desired shape, such as polyethylene, polypropylene or the like. It is presently preferred to use transparent low-density polyethylene to form nozzle 1, so that the consumer can see baffle member 10.

Baffle member 10 may be made from any porous material suitable for forming to the desired shape, such as porous plastic foams, porous cellulosic materials and the like. It is presently preferred to use a porous, rigid foam to form porous baffle member 10. However, flexible, soft foams can also be used.

To ensure that baffle member 10 is sealingly engaged in the nozzle 1, the base 12 sealingly engages inner wall 2a of nozzle 1. Accordingly, base 12 may be of slightly greater cross-section as inner wall 2a, so that the base is slightly compressed as it is forced into the nozzle 1 and beyond ribs 9. In this manner, whether the member 10 is made from a rigid or flexible foam, the base 12 will be urged into sealing engagement with inner wall 2a.

Nozzle 1 and baffle member 10 may be of any suitable length. For example, nozzle 1 may suitably have an overall length of about 5 inches and may suitably be provided with a baffle member 10 of about 2 to about 2½ inches. Alternatively, nozzle 1 may have an overall length of about 3½ inches and may be provided with a baffle member of about 1 to about 1½ inches. The selection of the length and diameter of the nozzle is not critical. The dimensions and porosity of the baffle member 10 will be empirically determined to provide the consumer with a nozzle and baffle member that will permit easy and convenient dispensing of the liquid from the squeeze bottle. The member 10 must not provide too much resistance to the flow of liquid therethrough as to require excessive squeezing forces on the bottle to dispense the liquid. A suitable baffle member 10 may be a sintered, high density polyethylene foam having pore sizes from about 5 to about 200 microns, preferably from about 80 to about 120 microns, and a void volume greater than about 40%, preferably from about 47 to about 53%.

We claim:

1. A douche vaginal nozzle, comprising an elongated hollow body having an open proximal end and a distal end, a plurality of apertures through said tubular body adjacent said distal end to permit liquid flowing, under initial pressure, through the interior of said tubular body toward said distal end to exit said nozzle, and an elongated baffle member, comprising a liquid permeable porous body, arranged inside said tubular body adjacent said apertures for regulating the flow of liquid exiting said nozzle, wherein said porous body comprises means to diffuse said flow of liquid, under said initial pressure, with a reduced pressure, to a gently flowing stream, and wherein said porous body comprises means to minimize suckback of liquid exiting said nozzle, when the initial pressure is released, said tubular body of said nozzle having an internally threaded open base portion at said proximal end for threaded attachment to a bottle filled with a liquid douche, and a plurality of spaced-apart grooves are formed on the exterior of said tubular body extending longitudinally from said open proximal end, across said based portion and to said distal end.

2. The nozzle according to claim 1, wherein said apertures are formed within said grooves.

* * * * *